(12) United States Patent
Schmitt

(10) Patent No.: US 6,994,724 B2
(45) Date of Patent: Feb. 7, 2006

(54) SOFT-TISSUE TUBULAR PROSTHESES WITH SEAMED TRANSITIONS

(75) Inventor: Peter J. Schmitt, Franklin Square, NY (US)

(73) Assignee: McMurray Fabrics, Inc., Aberdeen, NC (US)

( * ) Notice: Subject to any disclaimer, the term of this patent is extended or adjusted under 35 U.S.C. 154(b) by 178 days.

(21) Appl. No.: 09/999,437

(22) Filed: Nov. 15, 2001

(65) Prior Publication Data

US 2002/0058991 A1    May 16, 2002

Related U.S. Application Data

(60) Provisional application No. 60/254,949, filed on Dec. 12, 2000, provisional application No. 60/249,066, filed on Nov. 15, 2000, provisional application No. 60/248,989, filed on Nov. 15, 2000.

(51) Int. Cl.
*A61F 2/06* (2006.01)

(52) U.S. Cl. ............... 623/1.51; 623/1.3; 623/1.35; 139/387 R; 428/36.1; 428/57; 428/193

(58) Field of Classification Search ............ 139/383 R, 139/384 R, 387 R, 35, 54, 389, 349, 408; 66/169 R, 176, 179, 192, 195; 428/57, 36.1, 428/36.2, 192, 193; 623/12, 11.11, 1.1, 1.25, 623/1.35, 1.49, 1.5–1.54, 66.1, 901, 1.13, 623/1.3, 1.31, 1.44; 606/151–156, 191–200, 606/36

See application file for complete search history.

(56) References Cited

U.S. PATENT DOCUMENTS

| | | | |
|---|---|---|---|
| 444,880 A | 1/1891 | Erskine | |
| 2,729,958 A | * 1/1956 | Miles | .......................... 66/179 |
| 2,978,787 A | 4/1961 | Liebig | |
| 3,096,560 A | 7/1963 | Liebig | |
| 3,853,462 A | * 12/1974 | Smith | .......................... 8/130.1 |
| 3,945,052 A | 3/1976 | Liebig | |
| 4,166,463 A | * 9/1979 | Bloom | .......................... 602/63 |
| 4,668,545 A | 5/1987 | Lowe | |
| 4,771,518 A | 9/1988 | LaPointe et al. | |
| 4,822,371 A | * 4/1989 | Jolly et al. | ..................... 623/32 |
| 5,178,630 A | 1/1993 | Schmitt | |
| 5,282,846 A | 2/1994 | Schmitt | |
| 5,282,848 A | 2/1994 | Schmitt | |
| 5,370,682 A | 12/1994 | Schmitt | |
| 5,370,683 A | 12/1994 | Fontaine | |
| 5,385,580 A | 1/1995 | Schmitt | |
| 5,487,858 A | 1/1996 | Schmitt | |
| 5,509,931 A | 4/1996 | Schmitt | |

(Continued)

FOREIGN PATENT DOCUMENTS

DE    29 13 510 A1    10/1979

(Continued)

*Primary Examiner*—David J. Isabella
*Assistant Examiner*—Urmi Chattopadhyay
(74) *Attorney, Agent, or Firm*—Kilpatrick Stockton LLP

(57) ABSTRACT

Single tubular woven or bifurcated prostheses are disclosed having varying diameters and tapered transitions. The prostheses comprise a seam along the tapered edges, thereby providing a substantially fluid-tight transition between sections or extents of the prostheses. The seam may be located at an edge where fabric of the prosthesis tapers from one diameter to a different diameter and/or at a point where the prosthesis splits such as a bifurcation. The seamed crotch may be used for tapered and non-tapered bifurcated grafts. The seam may be woven directly on a weaving loom or joined together after weaving is completed.

18 Claims, 10 Drawing Sheets

U.S. PATENT DOCUMENTS

| | | |
|---|---|---|
| 5,697,970 A | 12/1997 | Schmitt et al. |
| 5,755,734 A * | 5/1998 | Richter et al. .............. 606/194 |
| 5,800,514 A | 9/1998 | Nuñez et al. |
| 5,904,714 A | 5/1999 | Nuñez et al. |
| 5,913,894 A | 6/1999 | Schmitt |
| 6,090,137 A | 7/2000 | Schmitt |
| 6,187,033 B1 * | 2/2001 | Schmitt et al. ............ 623/1.35 |
| 6,454,796 B1 * | 9/2002 | Barkman et al. .......... 623/1.35 |
| 6,592,539 B1 * | 7/2003 | Einarsson et al. ............ 602/62 |

FOREIGN PATENT DOCUMENTS

| | | |
|---|---|---|
| EP | 0 095 940 | 12/1983 |
| GB | 2 115 776 A | 9/1983 |
| JP | 03 045743 | 2/1991 |
| WO | WO 83/03349 | 10/1983 |
| WO | WO 88/06026 | 8/1988 |
| WO | WO 89/00031 | 1/1989 |
| WO | WO 97/43983 | 11/1997 |
| WO | WO 99/40875 | 8/1999 |
| WO | WO 02/027085 A3 | 4/2002 |

* cited by examiner

SOFT-TISSUE TUBULAR PROSTHESES WITH SEAMED TRANSITIONS

CROSS-REFERENCE TO RELATED APPLICATIONS

This application claims the benefit of U.S. Provisional Applications Ser. No. 60/248,989 filed Nov. 15, 2000; Ser. No. 60/249,066 filed Nov. 15, 2000; and Ser. No. 60/254,949 filed Dec. 12, 2000, which are incorporated by reference in their entirety.

FIELD OF THE INVENTION

The present invention relates to tubular prostheses, and more particularly to tubular prostheses having varying diameters and/or branching segments, and methods for their manufacture. The prostheses of the present invention are advantageous for use in implantable endoluminal applications.

BACKGROUND OF THE INVENTION

Tubular woven fabrics may be utilized for prostheses implantable in soft-tissue to replace or repair damaged or diseased vessels or passages in the body. A general discussion of different types of woven fabric prostheses is set forth in U.S. Pat. No. 5,800,514, issued Sep. 1, 1998, the disclosure of which is hereby incorporated herein by reference.

Applications for implantable prostheses include, but are not limited to, applications in the vascular system, urinary tract, gastrointestinal tract, endocrine system, and lymphatic system. In particular, endoprostheses are used in the vascular system to prevent blood flow from rupturing a weakened section of a vessel. Such endoluminal conduits are generally affixed in a specified location in a vessel by means of stents, hooks, and/or other mechanisms which serve to secure the device in place. Endoluminal tubular devices or conduits can also be used in other vessels and passages in the body, such as in the esophagus and colon.

Vascular grafts have been used successfully for many years to replace segments of a diseased vessel by open surgical methods. These techniques, however, require long and expensive procedures, which have a high degree of risk associated with them due to the complexity of the surgical procedures and risks of surgery in general. Presently, less invasive techniques for treating abnormal, diseased, and traumatized vessels have become more prominent because they present less risk to the patient and are less complex than open surgery. As an example of such a procedure, a physician will make an incision in the femoral artery and introduce an endoluminal device by means of a catheter delivery system to the precise location of the damaged or diseased vessel. The device generally includes a stent and graft combination, which is deployed from the delivery system and affixed in place usually by use of a balloon catheter. The balloon catheter is used to expand the stents which are attached to, and most often contained within, the graft portion. Expansion of the stent serves both to anchor the graft and to maintain the graft and the vessel lumen in an open state. In some cases, self-expanding stents or the like are used. Stents made from shape-memory materials, such as nitinol, are also employed, whereby radial expansion or contraction of the stent is designed to occur at specified temperatures.

Effective use of tubular endoluminal prostheses, however, requires a high degree of precision in the diameter of the tube, such that the outside diameter of the prosthesis matches the inside diameter of the body lumen very closely, thereby conforming the prosthesis to the internal surface of the vessel. Vessels and lumens in the body, however, often vary in diameter and shape from one point or segment to another. In addition, vessels sometimes define a tortuous path between two points along their length. This is particularly true with vessels in the vascular system. Thus, tubular endoprostheses which are generally singular in configuration cannot accurately conform to all portions of a vessel lumen which have such variations present. In an attempt to conform to a varying diameter and/or angled or ill-shaped vessel, a prosthesis wall will often require bunching, or gathering, within the lumen of the vessel. Bunching of a prosthesis wall into an unsmooth configuration generally creates a more turbulent environment for blood flow and presents an increased and long-term potential for thrombosis.

More recently, in recognition of certain problems in delivering and implanting endoluminal prostheses, a thinly woven graft was made, which is designed to closely fit the inner lumen of vessels. However, these grafts have been made in single lengths or bifurcated structures using traditional weaving techniques, which have specific limitations as to the final shape of the product. Also, in conventional weaving techniques, the transition from one diameter to another occurs at a single point in the weave, creating a sudden change in the weaving pattern of the fabric in bifurcated or multi-diameter grafts. Such sudden changes create voids and gaps in a prosthesis wall and are considered undesirable.

Conventional weaving processes are commonly employed to fabricate various tubular-shaped products. For example, implantable tubular prostheses which serve as conduits, such as vascular grafts, esophageal grafts, and the like, are commonly manufactured using tubular weaving techniques, wherein the tubular product is woven as a flat tube. In such weaving processes, yarns are interwoven in different directions to create the tubular fabric. For example, a set of warp yarns run lengthwise parallel to the selvages, or edge portions, and represent the width of the product being woven. Fill yarns run from selvage to selvage at right angles to the warp and are interlaced between the warp yarns. The fill yarn is woven along the length of the warp yarns, with each successive pass of the fill yarn across the warp yarns for each side of the tube representing one machine pick. Weaving one fill yarn along the entire circumference of the tube, i.e., one filling pick, requires two picks of the weaving machine. Thus, two machine picks represent one filling pick in a tubular woven structure. As such, in a conventional woven product, the fill yarn is woven along the length of the warp yarns for a multiple number of machine picks. The resulting woven product is defined in length by the number of filling picks of the fill yarn and defined in width by the number of warp yarns in which the fill yarn is woven between.

Conventional techniques of forming tubular shapes have required manual cutting and suturing of standard woven tubular prostheses to the desired size and shape. Woven tubular prostheses, such as vascular grafts, having tapered diameter sections or tailored shapes are typically made by manual customization in the form of cutting, splicing, and/or tailoring with sutures.

Conventional grafts having more than one diameter are made by weaving separate grafts having different diameters and suturing the individual grafts together to make a continuous tube. The change in diameter between graft segments requires customized cutting to gradually transition from one diameter to another. For example, a surgeon may select a bifurcated graft having a 24 mm aortic section and equivalent 12 mm femoral sections for use in a patient. If one of the patient's femoral arteries is 10 mm in diameter, the surgeon would manually cut the appropriate femoral section and suture a seam along that section to form a leg more closely matching a 10 mm diameter. This customization requires cutting and suturing. Such customization relies heavily on the skill of the physician and allows little quality control in the final product. Customized grafts may not always be made in advance for a particular patient, since the requirements for such customization may not be known until the physician begins the procedure to introduce the device into the body. Additionally, suture seams take up considerable amounts of space when packed into a delivery capsule or other catheter-like device designed to deploy endoluminal prostheses.

Thus, conventional continuously woven bifurcated grafts suffer the disadvantages of gaps created at the bifurcation point between the prosthesis trunk and leg portions due to separation or splitting of the warp yarns, and featuring only leg portions having equal diameters. Different diameter leg portions could be accomplished only through customization. Such customization often requires manually cutting off one leg portion and suturing onto the trunk of another independently formed leg having a different diameter.

Complex shapes, such as tubular "S-shaped" or frusto-conical-shaped woven sections have not been attempted using conventional weaving techniques due to the impractibility, intensive labor, and resulting high cost to the consumer. Indeed, such shaped tubes could not be woven practically using prior art techniques.

In addition to requiring manual cutting and sewing steps, manually customizing grafts often creates sutured seams that are disadvantageous in endoluminal prostheses, particularly because of the space that sutures occupy when tightly packed into a catheter delivery system. Furthermore, such seams disadvantageously contribute to irregularities in the surface of a graft, which may contact and possibly erode a weakened area of a vessel and/or increase the potential for thrombosis.

Recently, continuous flat-weaving techniques have been used to make graft diameter changes in a gradual manner, such that a tubular section transitions from one diameter to another diameter in a tapered fashion. U.S. Pat. No. 5,800,514 discloses a seamless tubular prosthesis and methods for producing seamless tubular prostheses. Techniques described in the patent permit the weaving of gradually-shaped tubular grafts in a continuous process to create seamless and void-free conduits for implantation in the body.

In general, U.S. Pat. No. 5,800,514 relates to flat-woven, implantable tubular prostheses, and in particular endoluminal grafts, which have been continuously woven to form seamless tubular products having gradual changes in diameter along their length. Such seamless grafts include tubular sections of various shapes formed from gradual changes in the number of warp yarns engaged or disengaged with the fill yarns during the weaving process. Changes in diameter and/or shape of a graft are accomplished by gradually engaging and/or disengaging selected warp yarns with the fill yarns in the weave pattern. Similarly, a bifurcation is achieved by disengaging selected warp yarns in the area of the intended split. The gradual transition can be accomplished using electronic jacquard looms controlled by computer software. Such engaging and/or disengaging of warp yarns can change the diameter of the tube or graft in a manner which creates a seamless and gradual transition from one diameter to another. Additionally, such engagement and/or disengagement can be used to create tubular vascular prostheses and the like which have any number of shapes.

Despite the potential advances achieved by such prostheses and techniques, such seamless prostheses have several disadvantages. In particular, the weaving techniques that are utilized to produce the prostheses and render them seamless, produce voids and gaps in the tubular wall.

Thus, there remains a need for developing tubular prostheses having smooth transitions from one diameter to another diameter that avoid gaps and voids in the tubular wall of the graft and provide an improved barrier against leakage in transition areas. There is a need for tubular prostheses having smooth transitions without voids and gaps at points of branching, such as in a bifurcated graft. There is also a need for tubular prostheses which allow for an increased rate of transition in tapered areas so as to provide more acutely angled transitions. There is also a need for tubular prostheses having smooth transitions that do not have excessive seams, such as with a seam sutured in the field. Further, there is also a need for tubular prostheses having smooth transitions that can be produced in various shapes in an efficient and economical manner.

SUMMARY OF THE INVENTION

The present invention provides a tubular woven prostheses, a single or bifurcated tube, that can be produced with varying diameters and tapered transitions. The tapered portions are closed by joining edges of the tapered transitional portions together. Prostheses of the present invention comprise a seam, in the form of a hem or selvage, along tapered edges that closes or seals the prostheses without the voids and gaps found in prior art prostheses. In an embodiment, edges are woven together into a stitched seam directly on a weaving loom. In other embodiments, a tubular prosthesis is formed on a weaving machine and the tapered portion, or extent, is left open, or unwoven, in non-tubular fashion. The edges are joined post-weaving to form a tubular article. In still other embodiments, prostheses of the present invention comprise a seam at the point of a furcation split or crotch that closes or seals the tube to provide a substantially fluid-tight transition without the voids and gaps found conventional prostheses.

In an embodiment of the present invention, a woven implantable tubular prosthesis is disclosed comprising: a plurality of warp yarns and fill yarns; a first tubular extent having a first diameter; a second tubular extent having a second diameter different from the first diameter, and the first and second tubular extents are spaced apart to define a transition tubular extent therebetween. The prosthesis further comprises a tapered edge along the transition tubular extent formed by a weaving pattern having a graduated change in the number of warp yarns; and a seam along the tapered edge, wherein the seam provides a substantially fluid-tight transition between the first tubular extent and the second tubular extent. As such, a tubular extent of one diameter may be joined to another tubular extent of a different diameter, connecting the two tubular extents with a tapered transition element. The seam comprises top layer warp yarns and bottom layer warp yarns woven together along the tapered edge on a weaving loom. The diameter of the first tubular extent and the diameter of the second tubular extent is each defined by a different number of warp yarns.

In other embodiments of the present invention, the first and second tubular extents are spaced apart to define an open transition extent therebetween. The prosthesis further comprises an unwoven tapered edge along the open transition extent formed by a weaving pattern having a graduated change in the number of warp yarns.

In other embodiments, the tubular prosthesis further comprises a plurality of secondary tubular extents, each woven at a transition with the first tubular extent; and an open crotch formed at the transition between the first tubular extent and the plurality of secondary tubular extents. The open crotch is formed by a weaving pattern that disengages a predetermined number of warp yarns along the transition. The prosthesis further comprises a seam along the crotch, wherein the seam provides the transition between the first tubular extent and the plurality of secondary tubular extents with a substantially fluid-tight closure. The plurality of secondary tubular extents may comprise a pair of secondary tubular extents defining a bifurcated structure. Each of the pair of secondary tubular extents may have a different diameter or the same diameter.

In embodiments, the graduated change in the number of warp yarns includes disengagement of predetermined warp yarns from the weaving pattern. The high ratio of disengaged warp yarns to fill yarns in the present invention allows the tapered edge in a tubular prosthesis to have an angle greater than 45 degrees. For example, the ratio of disengaged warp yarns to fill yarns can result in the tapered edge having approximately a 90 degree angle.

Embodiments of tubular prostheses in the present invention comprise various shapes, including a frustoconical shape, an "S" shape, an inward taper, and an outward flare, as well as other shapes needed for implantation in the body.

Prostheses of the present invention utilize various materials, depending on the intended use of the tubular prosthetic article. Such materials include warp yarns and fill yarns made from polyester, polypropylene, polyethylene, polyurethane, polytetrafluoroethylene, and mixtures thereof. Preferably, prostheses of the present invention are flat-woven.

In embodiments having an open transition extent and/or an open crotch, the seam includes a seam forming means to close the open transition extent into a tube after weaving is completed. The seam forming means comprises stitching sewn along the tapered edge, gluing, stapling, welding, and/or other means suitable for securely closing a tubular prosthesis seam.

In another aspect, the present invention includes a method of making a woven implantable tubular prosthesis, comprising: weaving a first tubular extent having a first diameter using a first predetermined number of warp yarns; weaving continuously from the first tubular extent a transition tubular extent formed by a weaving pattern having a graduated change in the first predetermined number of warp yarns to produce a tapered edge along the transition tubular extent; and weaving a second tubular extent continuously from the transition tubular extent using a second predetermined number of warp yarns. Such a method also includes creating a seam along the tapered edge, wherein the seam provides a substantially fluid-tight transition between the first tubular extent and the second tubular extent. Creating the seam further comprises weaving top layer warp yarns and bottom layer warp yarns together along the tapered edge on a weaving loom.

Methods of making a woven tubular prosthesis of the present invention include weaving a first tubular extent having a first diameter using a first predetermined number of warp yarns; weaving continuously from the first tubular extent an open transition extent formed by a weaving pattern having a graduated change in the first predetermined number of warp yarns to produce an unwoven tapered edge along the open transition extent; and weaving a second tubular extent continuously from the open transition extent using a second predetermined number of warp yarns. Such methods further include creating a seam along the tapered edge, wherein the seam provides a substantially fluid-tight transition between the first tubular extent and the second tubular extent. Embodiments of methods of the present invention include creating the seam using a seam forming means to close the open transition extent into a tube after weaving is completed. The seam forming means comprises sewing a seam along the tapered edge, or other means suitable for closing a seam on an implantable prosthesis.

Methods of the present invention also include making a woven tubular prosthesis, comprising: weaving a first tubular extent having a first diameter using a first predetermined number of warp yarns; weaving continuously from the first tubular extent an open transition formed by a weaving pattern that disengages a second predetermined number of warp yarns along the transition to produce an open crotch; and weaving a plurality of secondary tubular extents, each woven at a transition with the first tubular extent. Such methods also include creating a seam along the crotch, wherein the seam provides the transition between the first tubular extent and the plurality of secondary tubular extents with a substantially fluid-tight closure. Creating the seam further comprises using a seam forming means, such as sewing, to close the open crotch after weaving is completed. The seamed crotch may be used for tapered and non-tapered bifurcated grafts.

Tubular prostheses of the present invention differ from the tubular prostheses described in U.S. Pat. No. 5,800,514, insofar as the tubular prostheses of the present invention are not seamless. The seam portion in the tubular prostheses of the present invention is advantageous as it minimizes voids and gaps found along the tapered edges and at the bifurcation point of the tubular prostheses.

Features of a soft-tissue prosthesis with seamed transitions of the present invention may be accomplished singularly or in combination in one or more of the embodiments of the present invention. As will be appreciated by those of ordinary skill in the art, the present invention has wide utility in a number of applications as illustrated by the variety of features and advantages discussed below.

A tubular prosthesis of the present invention and methods for making same provide numerous advantages over prior art tubular prostheses and methods. For example, the present invention advantageously provides tubular woven single or bifurcated prostheses that can be produced with varying diameters and tapered transitions. As a result, the present invention advantageously provides tubular prostheses in complex shapes.

Another advantage is that the present invention provides methods for producing tubular prostheses having seams at tapered edges in transition areas that allow for an increased rate of transition. Seamed edges of tapered portions of prostheses of the present invention have advantages over the seamless edges of the prior art, as seamed edges provide an improved barrier against leakage. In addition, prostheses of the present invention may comprise more abruptly tapered portions than the prostheses of the prior art, rendering the prostheses of the present invention more suitable for use in certain applications.

Another advantage is that tubular prostheses of the present invention having seams at transition areas, such as tapers and furcations, provide increased strength to the graft in those areas.

Yet another advantage is that tubular prostheses made according to the present invention have more uniform characteristics such as porosity, strength, flexibility, and thickness along the length of the prosthesis Embodiments of the tubular prostheses of the present invention can be as implantable endoluminal prostheses in cardiovascular, gastrointestinal, genitourinary, gynecologic, hepatobiliary, endocrine, otolaryngologic, pulmonary, and other intra- and inter-organ tracts, pathways, and/or luminal communications in the body. The prostheses may be curved, tapered, or otherwise adapted for use in different luminal pathways. The methods of the present invention may also be advantageous for creating split tubular fabrics for other applications.

As will be realized by those of skill in the art, many different embodiments of the tubular prosthesis of the present invention are possible. Additional uses, objects, advantages, and novel features of the invention are set forth in the detailed description that follows and will become more apparent to those skilled in the art upon examination of the following or by practice of the invention.

DETAILED DESCRIPTION OF THE INVENTION

Embodiments of the present invention comprise a woven implantable tubular prosthesis having varying diameters and tapered transitions including a seam formed along a tapered edge or opening in a transition area. Seams of the present invention provide a substantially fluid-tight transition between a first tubular portion, or extent, and a second tubular extent. The seam may be located at an edge where fabric of the prosthesis tapers from one diameter to a different diameter and/or at a point where the prosthesis splits, such as with a bifurcation. An edge is defined as an outer limit of the graft width as taken along the longitudinal axis as the graft is flat-woven on the loom. In embodiments, the seam is stitched directly on a weaving loom by stitching the top and bottom fabric portions of a tubular prosthesis together. In other embodiments, the seam is joined together after weaving is completed.

Figure 1:
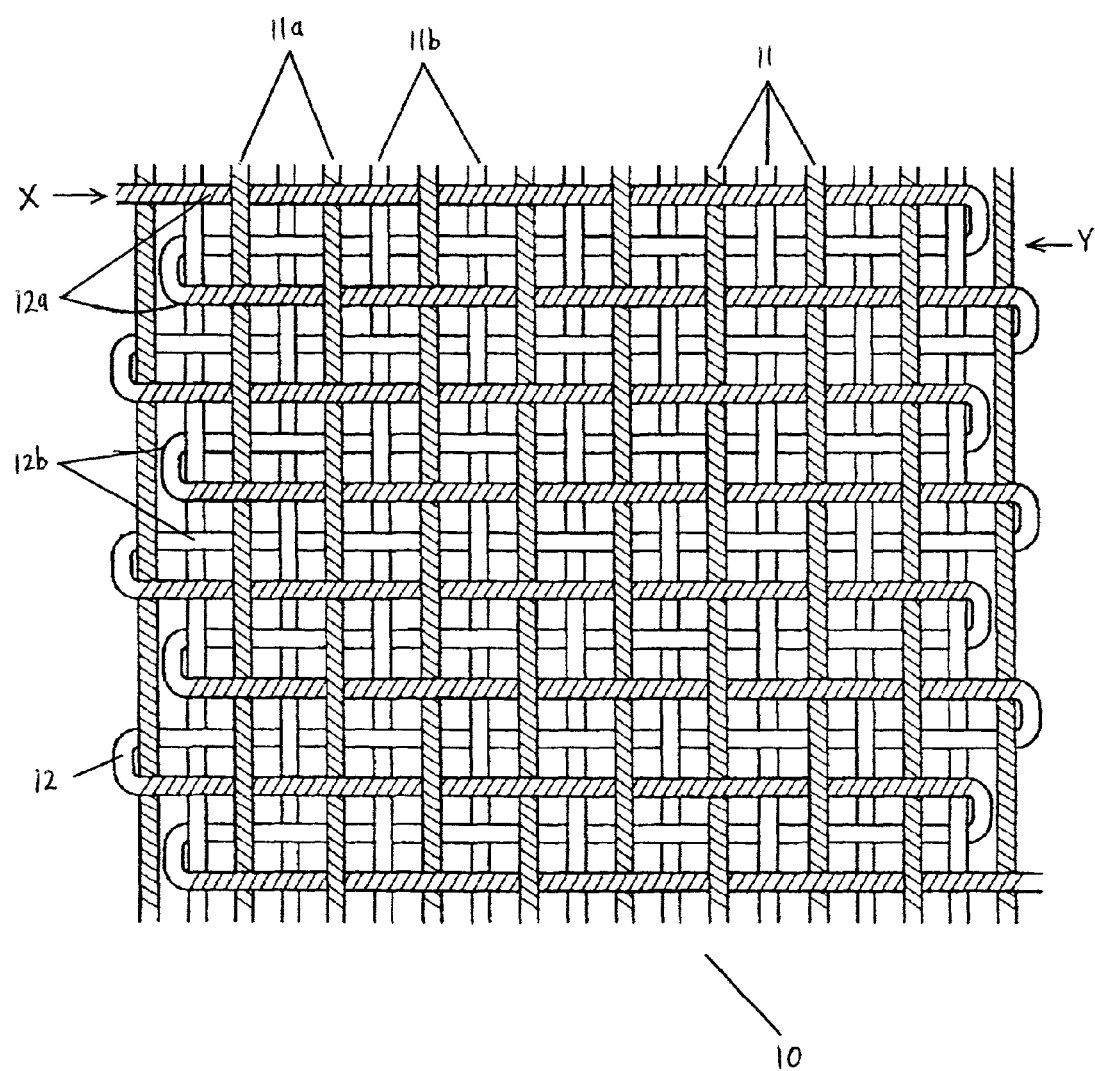
FIG. 1 is a weaving schematic showing a conventional plain tubular weave pattern known in the art.

Conventional weaving techniques can be incorporated in methods for producing embodiments of tubular prostheses of the present invention. Referring to the Figures, FIG. 1 shows a conventional plain tubular weave pattern 10 known in the art. Warp yarns 11 are further shown as 11a indicating they are in the top layer of the weave and 11b indicating their presence in the bottom layer of the weave. Top layer warp yarns 11a and bottom layer warp yarns 11b run in a lengthwise direction in the graft and define the width of the graft. Fill yarns 12 are further shown as top fill yarns 12a and bottom fill yarns 12b. These fill yarns are woven with the top and bottom warp yarns 11a and 11b as shown in FIG. 1 in a manner known in the art. For example, a filling yarn shuttle (not shown) passes across warp yarns 11 while selected warp yarns 11 are lifted according to a specific weave pattern. In electronic weaving machines, such weave patterns can be programmed into the machine using software. In a typical plain tubular weave as depicted in FIG. 1, the shuttle first weaves top fill yarn 12a by passing across warp yarns 11 while certain warp yarns 11 are lifted. During travel of top fill yarns 12a, in direction X, for weaving of the top tubular body portion, the bottom warp yarns 11b are not lifted so as to prevent top fill yarns 12a from interweaving with bottom warp yarns 11b. Likewise, during passage of bottom fill yarns 12b, in direction Y, for weaving of the bottom tubular body portion, the top warp yarns 11a are always lifted such that bottom fill yarns 12b are not interwoven with top warp yarns 11a. The plain tubular weave pattern as just described can be used to form single portions of tubular prosthetic grafts of the present invention that have a constant diameter. This pattern is then modified by gradually engaging or disengaging warp yarns to create tapers and/or shapes.

Figure 2:
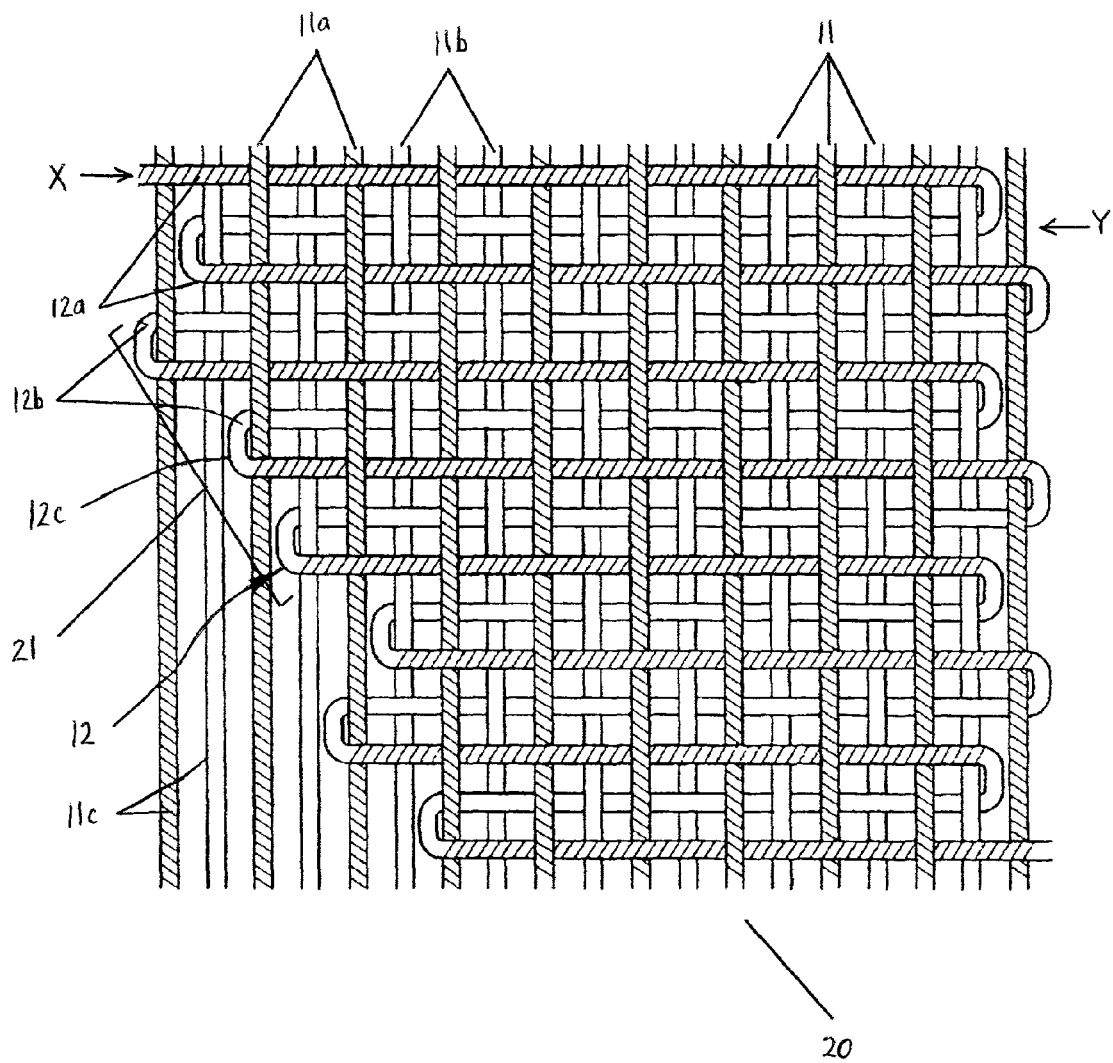
FIG. 2 is a weaving schematic depicting a prior art weaving pattern used in producing a tapered edge in a seamless tubular prosthesis.

FIG. 2 is a weaving schematic depicting a prior art weaving pattern 20 used in producing a seamless tubular prosthesis, according to a technique set forth in U.S. Pat. No. 5,800,514 for producing a tapered edge in a tubular woven article. As shown in FIG. 2, the tapered edge 21 is formed by gradually disengaging the warp yarns 11a and 11b. Disengaging the warp yarns 11a and 11b is accomplished by dropping the desired warp yarns, for example warp yarns 11c, such that the fill yarns 12 are not interwoven across the warp yarns 11 for that section of the pattern. This technique produces a tapered edge like tapered edge 21 in a tubular article. This type of dropping of warp yarns in a gradual manner forms the transitional portion of the graft. In continuous flat-weaving processes, the warp yarns are then re-engaged during the weave pattern once the transitional section has been completed.

As described, in the embodiments of the present invention, transition from one diameter to another diameter is accomplished by engaging and/or disengaging predetermined warp yarns from the weave pattern. Such disengaging or engaging of warp yarns can be gradual. However, such a transition can potentially be accomplished using any combination of numbers of warp yarns and fill yarns. A disadvantage of this recently developed technique is that in seamless tubular prostheses, the total number of warp yarns engaged and/or disengaged should not exceed a maximum of three warp yarns per four machine picks on each edge of the tubular flat-woven product in order to avoid gaps and voids at the transition. Tubular prostheses of the present invention eliminate this limitation on the rate of transition and the shallow angles resulting from such a gradual transition in seamless tubular prostheses.

Figure 3:
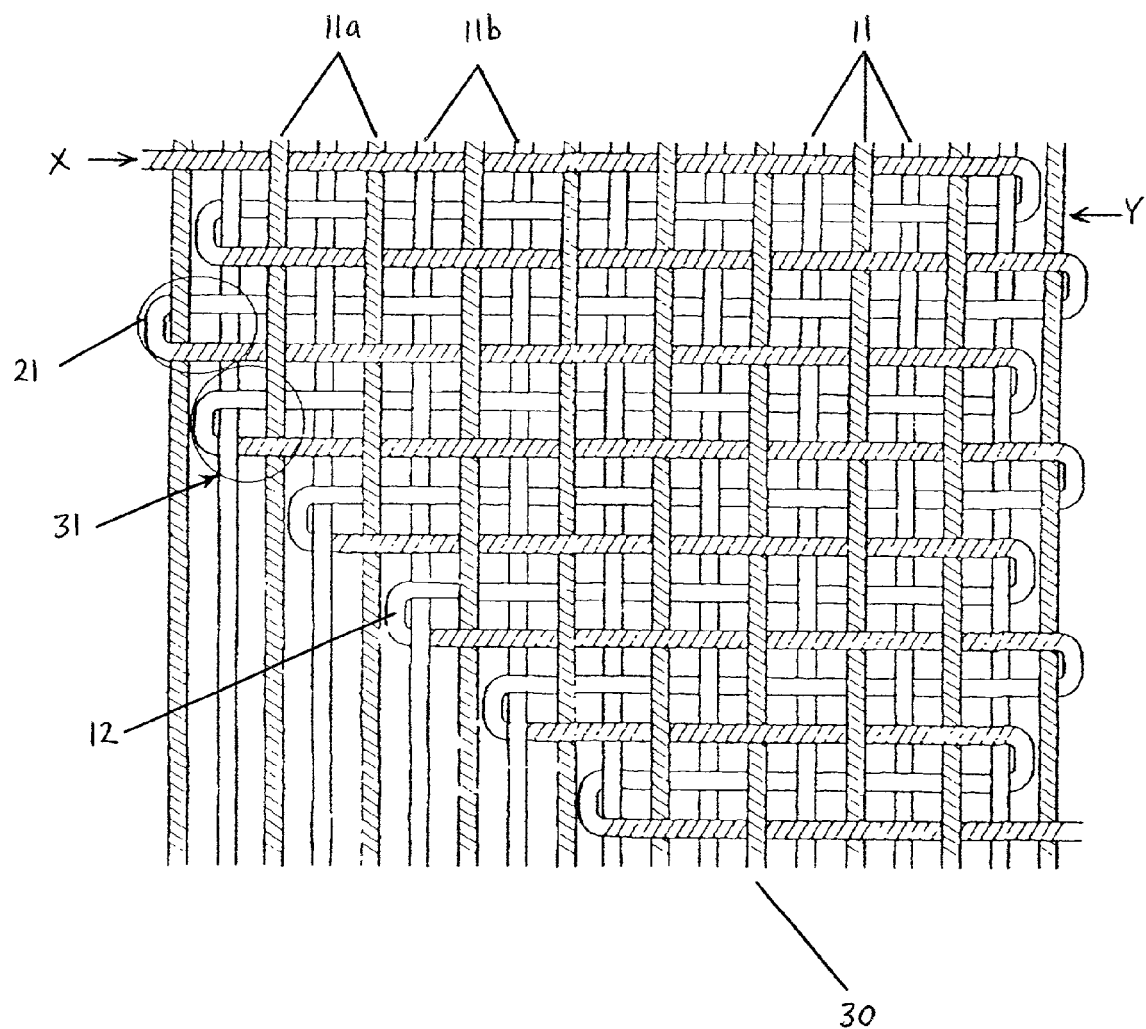
FIG. 3 shows a woven seam weave pattern utilized in a method of the present invention to produce a tapered edge in a tubular prosthetic article in an embodiment of the present invention.

FIG. 3 shows a woven seam weave pattern 30 utilized in a method of the present invention to produce the edge 21 of a tubular prosthetic article in an embodiment of the present invention. As shown in FIG. 3, the tapered tubular edge 21 is formed by interweaving top layer warp yarns 11a and bottom layer warp yarns 11b together to form a seam, or "selvage," comprising a single layer fabric at the tapered edge 21. A minimum of one warp yarn from each of the top and bottom layers is utilized to form the woven seam 31. Additional warp yarns from either or both layers may be utilized to increase the width of the seam 31. The greater the number of warp yarns utilized the greater the size, or width, of the seam. In embodiments of the present invention, the size of the seam may be varied depending the intended end use of the tubular article. In embodiments utilizing a woven seam, as shown in FIG. 3, the seam can be made while the tubular prosthesis is still on the weaving loom.

Figure 4:
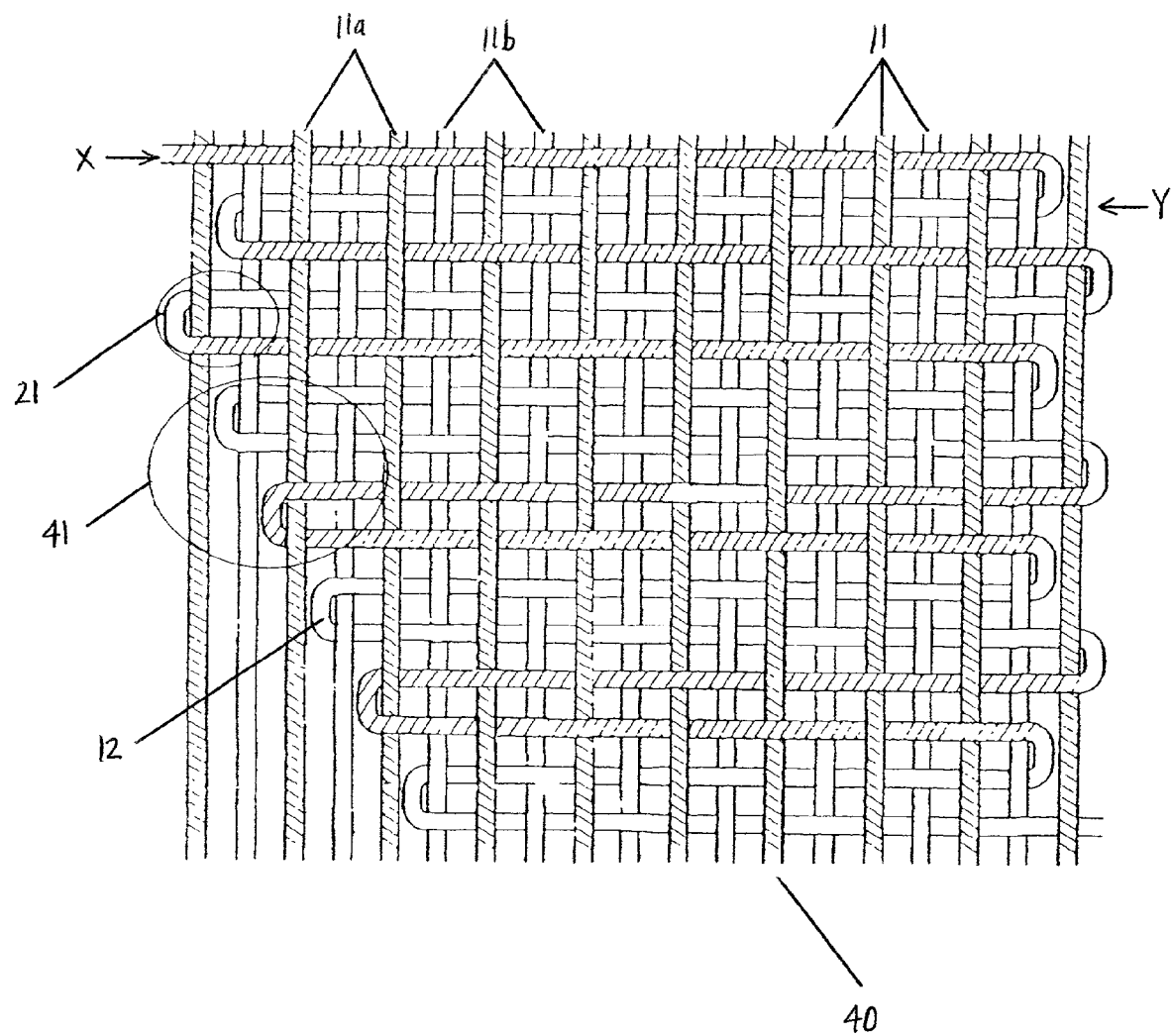
FIG. 4 shows an open edge weave pattern utilized in a method of the present invention to produce an open edge in a tubular prosthetic article in an embodiment of the present invention.

FIG. 4 shows an open edge weave pattern 40 utilized in a method of the present invention to produce an open edge 41 in a tubular article in an embodiment of the present invention. As shown in FIG. 4, the open tapered edge 41 is formed by causing the fill yarns 12 to remain on the same layer, either top or bottom, at the tapered tubular edge 21. In embodiments utilizing an open edge weave pattern, as shown in FIG. 4, a seam is generally made after weaving is complete and the prosthesis is removed from the loom. The tapered edges may be sealed by sewing, welding, bonding, gluing, stapling, and/or other techniques suitable for sealing tubular prosthetic articles.

Figure 5:
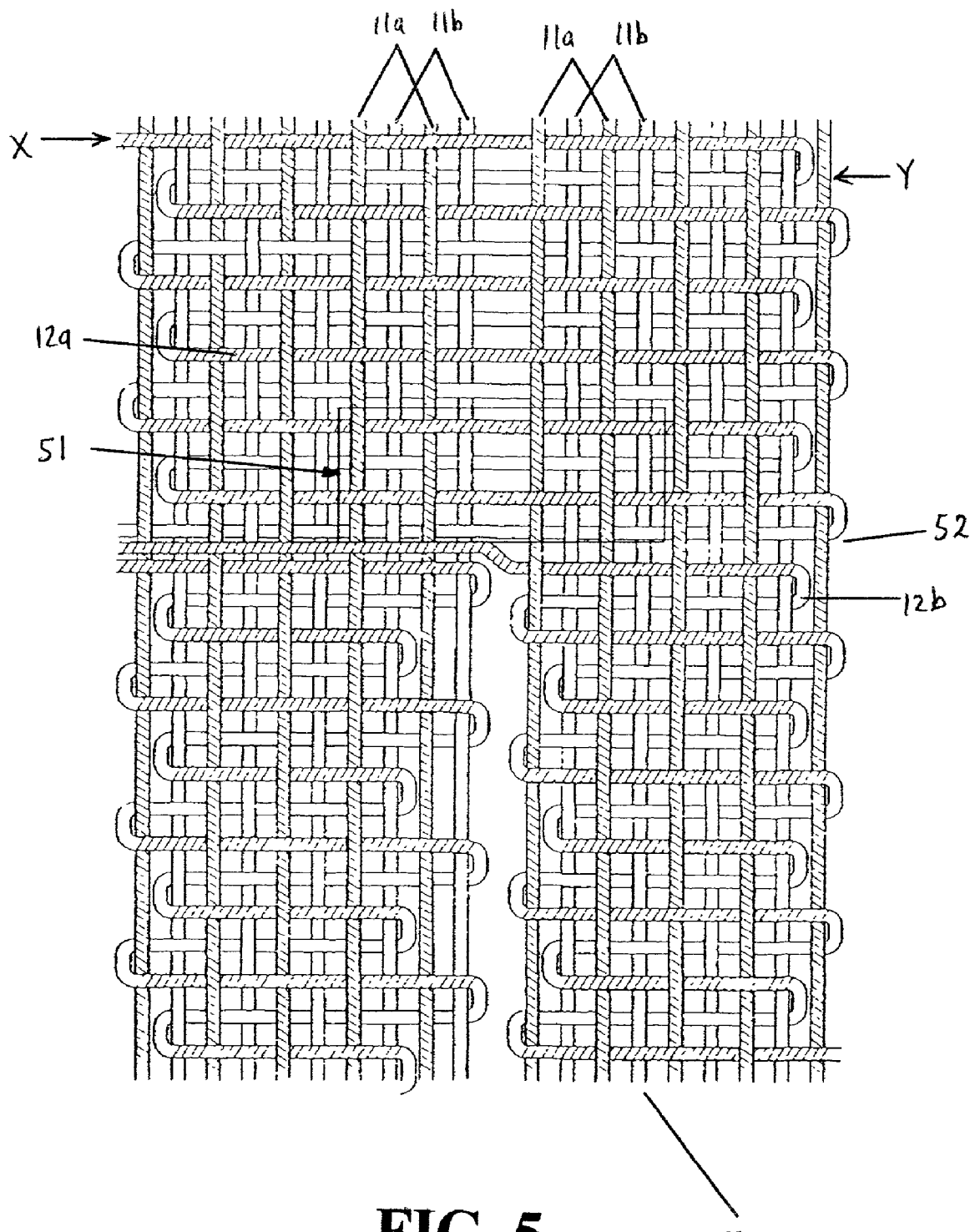
FIG. 5 shows an open crotch weave pattern that produces a tapered edge at a split in a prior art technique for making a tubular prosthesis.

FIG. 5 is an open crotch weave pattern 50 that produces a tapered edge at a split in a prior art technique for making a tubular prosthesis as set forth in U.S. Pat. No. 5,800,514, for producing a tapered edge in a tubular woven article. As shown in FIG. 5, the open crotch 51 at the bifurcation area 52 is formed by gradually disengaging warp yarns 11a and 11b from fill yarns 12a. and 12b. The disengaging of the warp yarns 11a and 11b is accomplished by dropping the desired warp yarns 11a and 11b from the end of the tubular flat-woven graft such that the fill yarns 12a and 12b are not interwoven across the warp yarns 11a and 11b for that section of the pattern. Using this technique, a transition at the bifurcation area 52 is limited to a maximum disengagement rate of three warp yarns per four machine picks.

Figure 13:
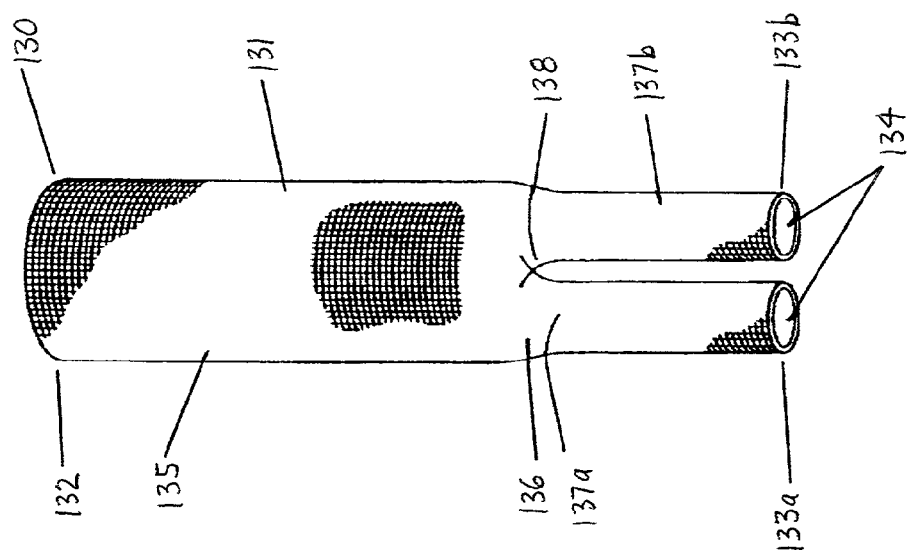
FIG. 13 is a view of a bifurcated tubular prosthesis in an embodiment of the present invention.

As shown in FIG. 5, in conventional manufacturing processes for tubular weaving of bifurcated grafts, it is necessary to split the number of warp yarns at the crotch area during the weaving process in order to split the tubular woven graft from a first tubular woven extent, such as a first aortic woven extent, into a plurality of secondary woven extents, such as first and second iliac woven extents. This splitting of warp yarns is necessary in order to accomplish the transition at the crotch 138, as shown in FIG. 13, where the diameter of the graft transitions from a first inner diameter of the aortic woven extent 135, to two separate inner diameters representing the first and second iliac woven extents 137a and 137b.

Figure 6:
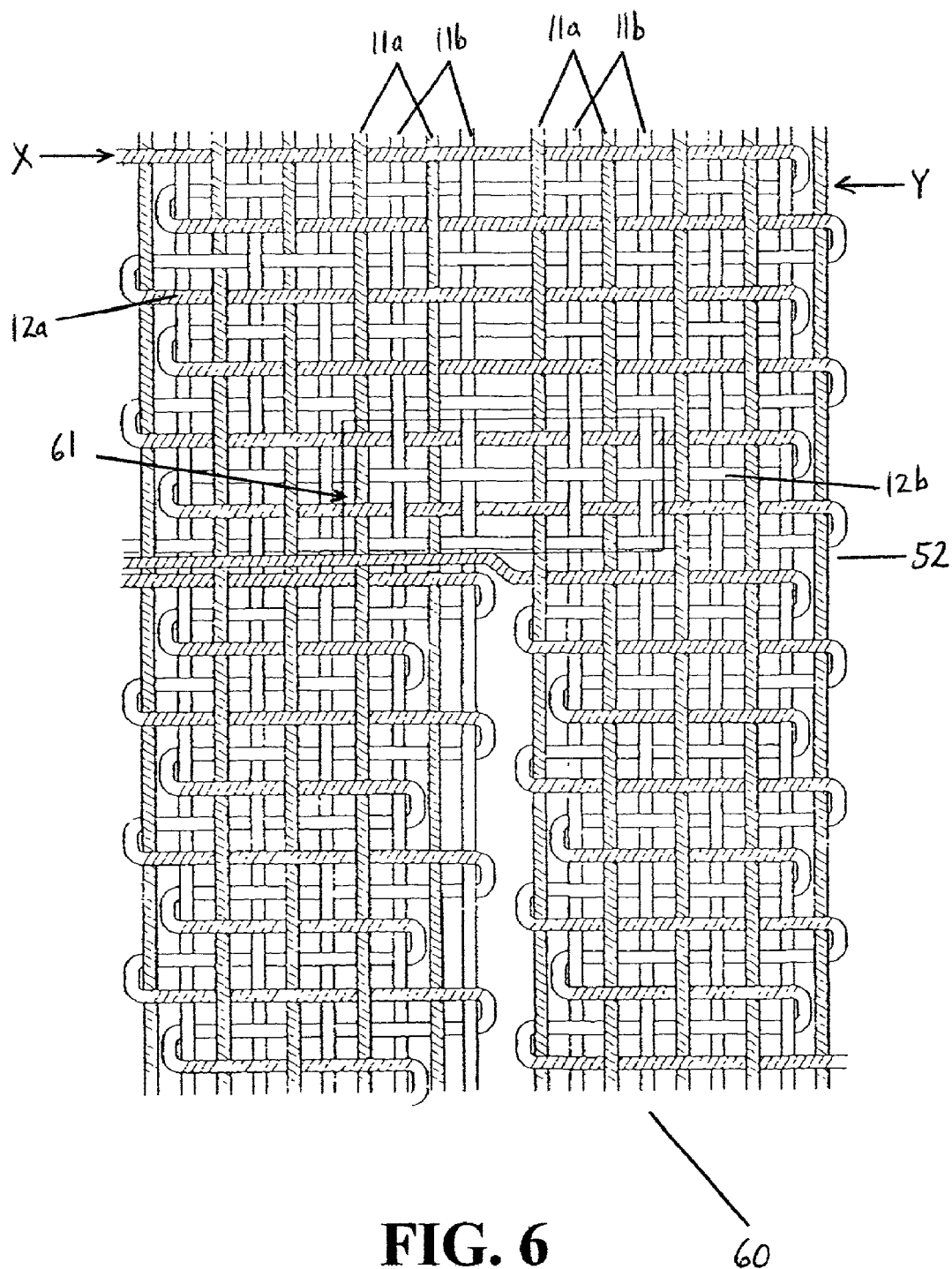
FIG. 6 shows a stitched crotch weave pattern utilized in a method of the present invention to produce a stitched crotch in a tubular prosthetic article in an embodiment of the present invention.

FIG. 6 is a stitched crotch weave pattern 60 utilized in a method of the present invention to produce a stitched crotch 61 in a tubular article in an embodiment of the present invention. As shown in FIG. 6, the bifurcation area 52 is formed by interweaving top layer warp yarns 11a and bottom layer warp yarns 11b together with fill yarns 12a and 12b to form a seam, or "selvage," comprising a single layer fabric at the bifurcation edges. A minimum of one warp yarn from each layer is utilized. Additional warp yarns from either or both layers may be utilized to increase the width of the seam. The greater the number of warp yarns utilized the greater the width, or size, of the seam. In embodiments of the present invention, the size of the seam may be varied depending the intended end use of the tubular article.

In embodiments utilizing a stitched crotch weave pattern 60 as shown in FIG. 4, a seam is generally made after weaving is complete and the prosthesis is removed from the loom. The edges at a crotch or bifurcation may be sealed by sewing, welding, bonding, gluing, stapling, and/or other techniques suitable for sealing tubular prosthetic articles.

FIGS. 7–14 illustrate tubular prostheses having various shapes and configurations in embodiments of the present invention. The weaving pattern is not shown to scale and the tapered portions comprise seams according to the present invention.

Figure 7:
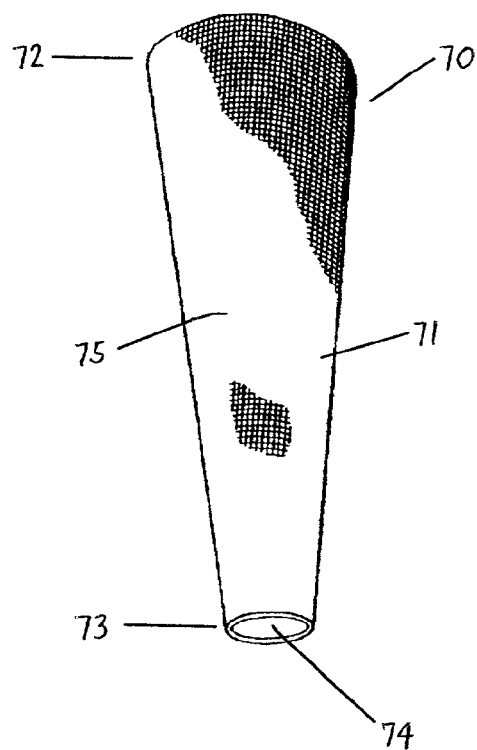
FIG. 7 is a view of a frustoconical-shaped tubular prosthesis in an embodiment of the present invention.

Referring to FIG. 7, a typical tubular woven textile graft 70 in accordance with the present invention is shown generally as a tapered graft in a generally frustoconical shape. Graft 70 is a textile product formed of a woven synthetic fabric. Graft 70 is depicted in one embodiment in FIG. 7 which includes a generally tubular body 71 having a first end 72 and an opposed second end 73, defining therebetween an inner lumen 74 which permits passage of blood through graft 70. Graft 70 includes continuous transitional woven extent 75 extending between first end 72 and second end 73, and extending along the entire length of graft 70. Graft 70 of FIG. 7 has a generally frustoconical shape, with first end 72 having a first tubular inner diameter and second end 73 having a second tubular inner diameter which is different than the inner diameter of first end 72. For example, first end 72 may have an inner diameter of 12 millimeters and second end 73 may have an inner diameter of 10 millimeters, with transitional woven portion 75 forming a gradual taper having successive changes in diameter throughout. As such, graft 70 gradually tapers from the 12 millimeter inner diameter of first end 72 to the 10 millimeter inner diameter of second end 73 along the length of transitional woven portion 75. The gradual tapering of transitional woven extent 75 is accomplished by gradually disengaging and/or engaging a selected number of warp yarns from the weaving pattern during weaving of the graft. Transitional woven extent 75 may include a seam along tapered edges to provide a substantially fluid-tight transition between first end 72 and second end 73.

Figure 8:
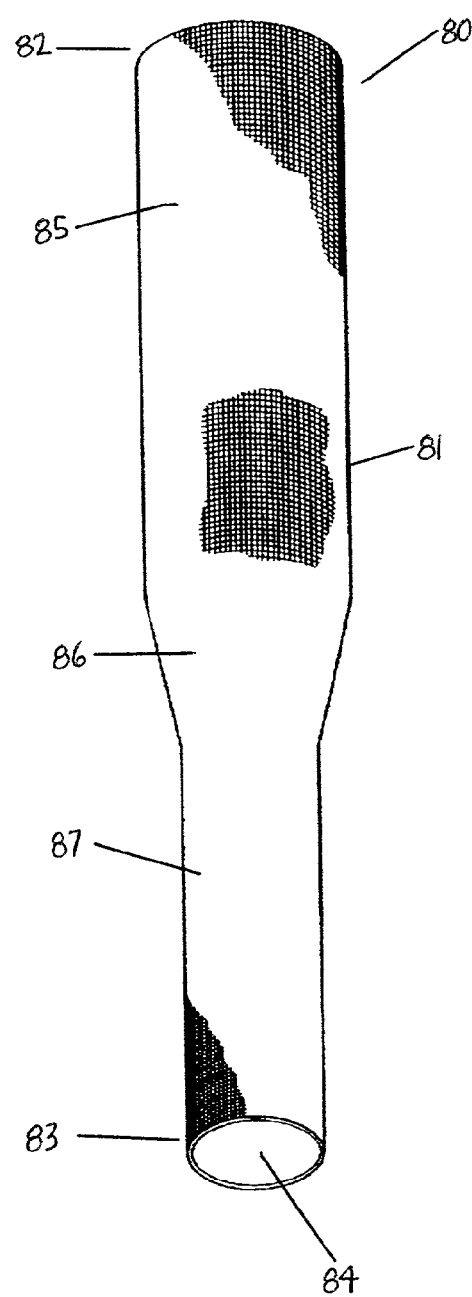
FIG. 8 is a view of another shape of a tubular prosthesis in an embodiment of the present invention.

FIG. 8 shows a variation of the configuration of FIG. 7, with graft 80 in the form of a step-tapered graft having a tubular body 81 with a first end 82 and an opposed second end 83 defining an inner lumen 84 therebetween. In the embodiment of FIG. 8, graft 80 includes first woven extent 85 which defines a portion of tubular body 81 having a continuous first inner diameter and second woven extent 87 which defines a portion of tubular body 81 having a continuous second inner diameter which is different than the inner diameter of first woven extent 85. Graft 80 of FIG. 8 further includes transitional woven extent 86 adjacent and contiguous with first and second woven extents 85 and 87. In such an embodiment, graft 80 includes a constant diameter extending through first woven extent 85 and a constant diameter which is different than the inner diameter of first woven extent 85 which extends through second woven extent 87, and gradually tapers from the inner diameter of first woven extent 85 to the inner diameter of second woven extent 87 through the length of transitional woven extent 86. Transitional woven extent 86 may include a seam along tapered edges to provide a substantially fluid-tight transition between first woven extent 85 and second woven extent 87.

Figure 9:
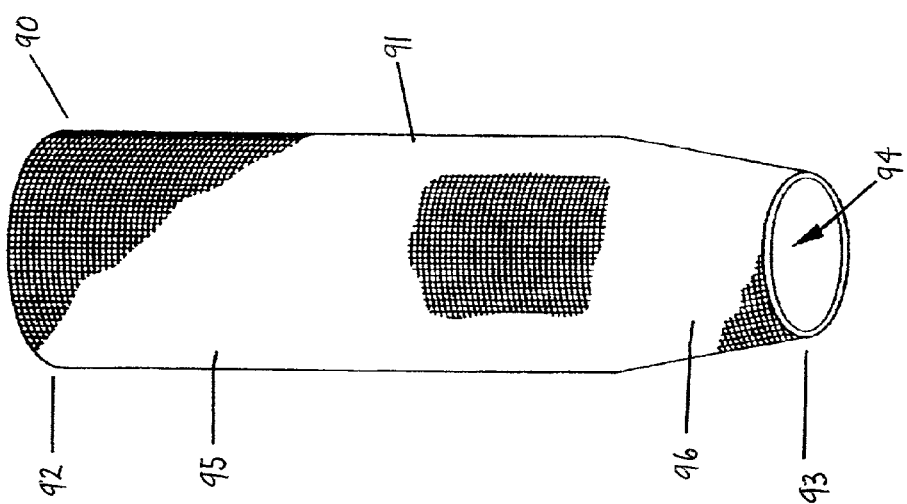
FIG. 9 is a view of another shape of a tubular prosthesis in an embodiment of the present invention.

FIG. 9 shows another embodiment of the step-tapered configuration of FIG. 8, with graft 90 having a tubular body 91 with a first end 92 and an opposed second end 93 defining an inner lumen 94 therebetween. In the embodiment of FIG. 9, graft 90 includes a first woven extent 95 and a transitional woven extent 96, with the first woven extent 95 defining first end 92 and including a continuous inner diameter along the length thereof, and the transitional woven extent 96 defining second end 93 and including a gradual taper such that graft 90 gradually tapers from the inner diameter of first woven extent 95 to a second diameter at second end 93 which is different than the inner diameter of first woven extent 95. It is contemplated that such gradual tapering can be either an inward taper or an outward, or flared, taper. Transitional woven extent 96 may include a seam along tapered edges to provide a substantially fluid-tight transition between first woven extent 95 and second end 93.

Figure 10:
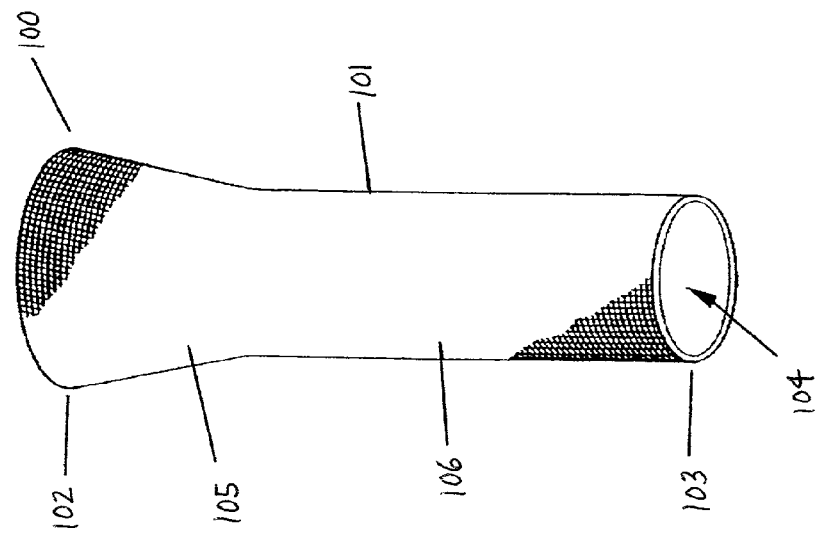
FIG. 10 is a view of another shape of a tubular prosthesis in an embodiment of the present invention.

FIG. 10 shows another embodiment of the configuration of graft 70 of FIG. 7, with graft 100 having a tubular body 101 with a first end 102 and an opposed second end 103 defining an inner lumen 104 therebetween. In the embodiment of FIG. 10, graft 100 includes a transitional woven extent 105 and a second woven extent 106, with the transitional woven extent 105 defining first end 102 and the second woven extent 106 including a continuous inner diameter along the length thereof, and defining second end 103. Further, transitional woven extent 105 includes a gradual taper such that graft 100 gradually tapers outwardly from the inner diameter of first end 102 to a second diameter at second end 103 which is different than the inner diameter of first end 102. Transitional woven extent 105 may include a seam along tapered edges to provide a substantially fluid-tight transition between first end 102 and second woven extent 106.

Figure 11:
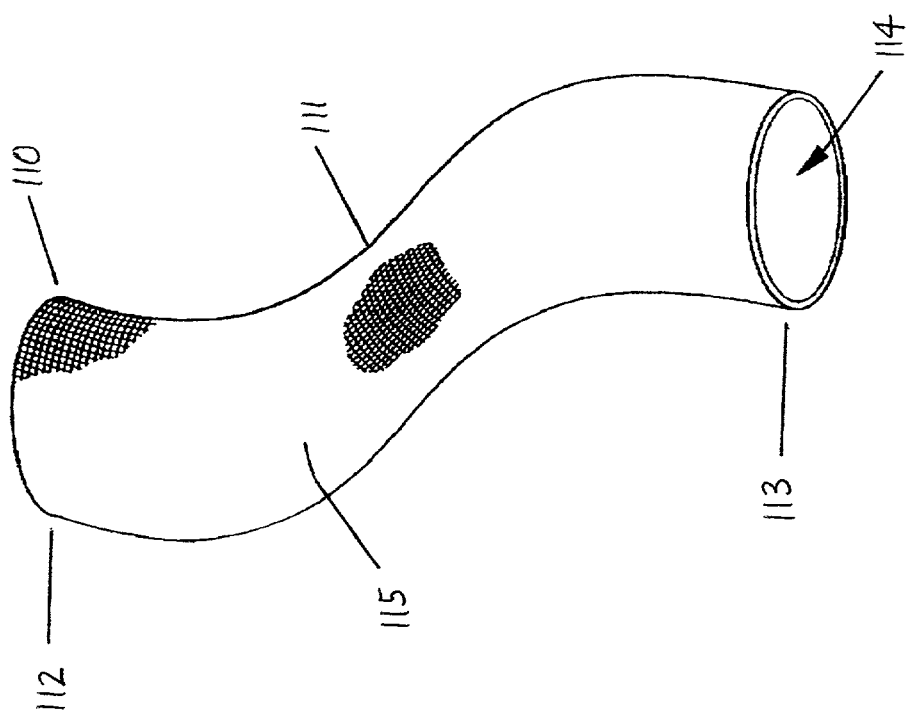
FIG. 11 is a view of a sinusoid-shaped tubular prosthesis in an embodiment of the present invention.

FIG. 11 depicts a sinusoidal shaped graft 110 having a tubular body 111 with a first end 112 and an opposed second end 113 defining an inner lumen 114 therebetween. In the embodiment of FIG. 11, graft 110 includes a continuous first woven extent 115, with the first woven extent 115 defining both first and second ends 112 and 113. First woven extent 115 has a continuous inner diameter along the length thereof, such that first end 112 and second end 113 have the same inner diameter. Graft 110 is shaped along its length in an "S" configuration, with tubular body 111 gradually changing direction as warp yarns on one edge of graft 110 during the weaving process are engaged or disengaged while the same portion of tubular body 111 on the other edge of graft 110 equally changes in the same direction as warp yarns are engaged or disengaged at this edge. Thus, as warp yarns at one edge of the graft are disengaged as that edge and shape of the graft gradually curve, the corresponding warp yarns at the opposite edge on the same pick are engaged. As the "S" shape again changes direction, the opposite may be true, that is, warp yarns at a given pick on one edge may be engaging as corresponding warp yarns at the other edge on the same pick may be disengaging. In order to maintain a constant diameter, the warp yarns at each of the edges of the tubular graft must simultaneously change by additionally adding or engaging an equal number of warp yarns on one edge as the other edge loses or disengages warps. Thus, the total number of warp yarns within the tubular body wall remains constant during the weaving process. Continuous first woven extent 115 may include a seam along tapered edges to provide a substantially fluid-tight transition between first end 112 and second end 113.

Figure 12:
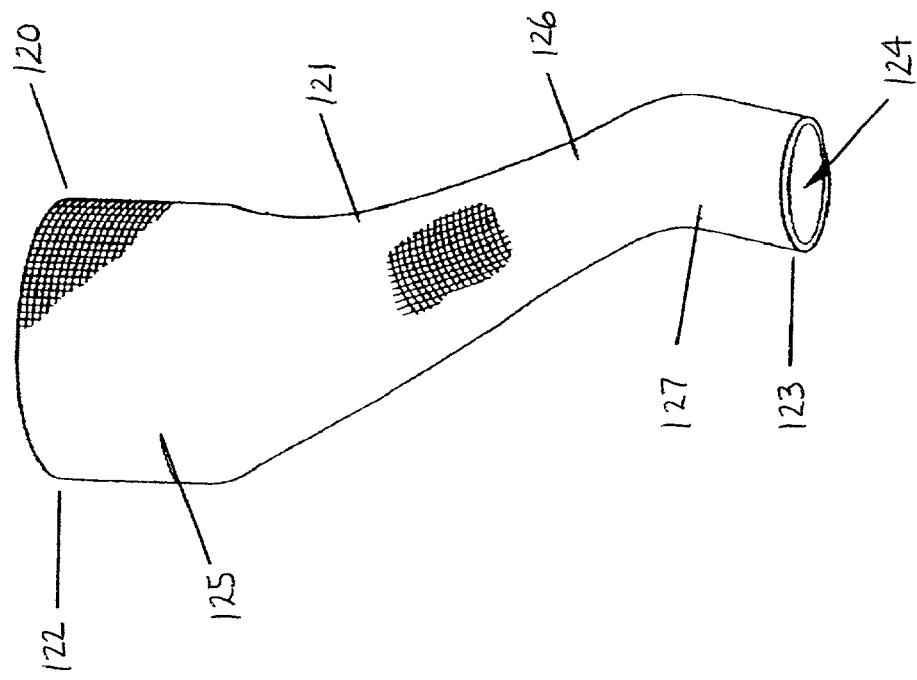
FIG. 12 is a view of another shape of a tubular prosthesis in an embodiment of the present invention.

FIG. 12 shows an embodiment of the present invention having a variation of the sinusoidal-shaped graft 110 shown in FIG. 11. Graft 120 in FIG. 12 includes a tubular body 121 with a first end 122 and an opposed second end 123 defining an inner lumen 124 therebetween. In the embodiment of FIG. 7, graft 120 includes first woven extent 125 having a first inner diameter and second woven extent 127 having a second inner diameter which is different than the inner diameter of first woven extent 125. Graft 120 further includes a transitional woven extent 126 adjacent first and second woven extents 125 and 127. For example, first woven extent 125 may include a woven graft section having an inner diameter of 12 millimeters and second woven extent 127 may include a woven graft section having an inner diameter of 10 millimeters, with transitional woven extent 126 forming a gradual taper. As such, graft 120 gradually tapers from the 12 millimeter inner diameter of first woven extent 125 to the 10 millimeter inner diameter of second woven extent 127 along the length of transitional woven extent 126. Graft 120 is shaped along its length in an "S" configuration similar to the manner in FIG. 11, with tubular body 121 gradually tapering in on one side of graft 120 during the weaving process, while the same portion of tubular body 121 on the other side of graft 120 tapers outwardly. Transitional woven extent 126 may include a seam along tapered edges to provide a substantially fluid-tight transition between first woven extent 125 and second woven extent 127.

Figure 14:
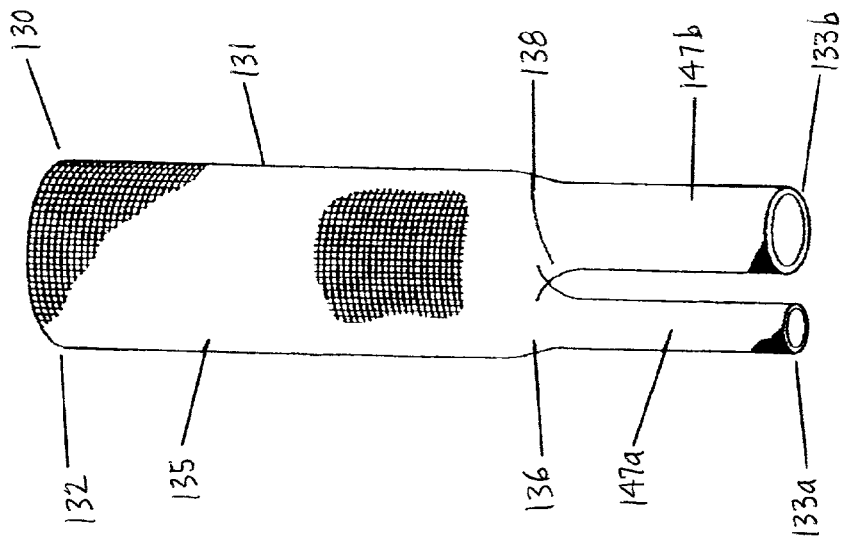
FIG. 14 is a view of another bifurcated tubular prosthesis in an embodiment of the present invention.

FIGS. 13 and 14 illustrate embodiments of tubular prostheses of the present invention comprising bifurcations. Referring to FIGS. 13 and 14, a typical tubular woven bifurcated graft 130 includes a generally tubular body 131 having a first end 132 and opposed second ends 133*a* and 133*b*, defining therebetween an inner lumen 134 which permits passage of blood once the bifurcated graft 130 is implanted in a blood vessel. Bifurcated graft 130 includes aortic woven extent 135 having a first inner diameter, and further includes first and second iliac woven tubular extents 137*a* and 137*b*, each having an inner diameter which is different than the inner diameter of aortic woven extent 135. The inner diameters of first and second iliac woven extents 137*a* and 137*b* can be the same as depicted in FIG. 13, or can be different as depicted in 147*a* and 147*b* of FIG. 14. Further, iliac woven extents 137*a* and 137*b* can be of the same general length as shown in FIGS. 13 and 14 or can be of different general lengths. Bifurcated graft 130 further includes bifurcated transitional woven extent 136 contiguous with aortic woven extent 135 and first and second iliac woven extents 137*a* and 137*b* at crotch 138, forming a bifurcated arch. Bifurcated transitional woven extent 136 forms a gradual taper such that bifurcated graft 130 gradually tapers from the inner diameter of aortic woven extent 135 to the inner diameters of first and second iliac woven extents 137*a* and 137*b* along the length of bifurcated transitional woven extent 136. The gradual tapering of bifurcated transitional woven extent 136 is accomplished by gradually disengaging and/or engaging a predetermined number of warp yarns from the weaving pattern during weaving of the graft, as discussed above. Bifurcated transitional woven extent 136 may include a seam along tapered edges to provide a substantially fluid-tight transition between aortic woven extent 135 and first and second iliac tubular extents 137*a* and 137*b*.

Further, during weaving of bifurcated graft 130, two separate filling yarn shuttles (not shown) are required for weaving of the two distinct iliac woven extents 137*a* and 137*b*. To form the gradual transition in the crotch 138, the shuttle designated for weaving of iliac woven extent 137*a* selectively and gradually engages warp yarns designated for weaving of iliac woven extent 137*b*. Likewise, the shuttle designated for weaving iliac woven extent 137*b* selectively and gradually engages warp yarns designated for weaving of iliac woven extent 137*a*. In this manner, the crotch 138 is woven using a simultaneous tapering effect at the interface between the aortic woven extent 135 and iliac woven extents 137*a* and 137*b*. As such, a smooth contiguous surface transition is obtained.

While a variety of shapes and configurations are shown in the drawings and described herein, any tubular, flat-woven graft incorporating a gradually transitioning, continuously woven portion is contemplated by the present invention. The gradual tapering of the transitional woven portion or extent is accomplished in each of the embodiments by gradually disengaging and/or engaging a predetermined number of warp yarns from the weaving pattern during weaving of the graft as discussed above.

Any type of textile product can be used as the warp yarns and fill yarns of the present invention. Of particular usefulness in forming the woven prostheses of the present invention are synthetic materials such as thermoplastic polymers. Thermoplastic yarns suitable for use in the present invention include polyesters, polypropylenes, polyethylenes, polyurethanes, polytetrafluoroethylenes, as well as others. The yarns may be of the monofilament, multifilament, or spun type.

Yarns utilized in prostheses of the present invention comprise yarns known and generally utilized in the art for prostheses. In general, the selection of yarn will depend on the intended end use application of the tubular prosthesis. Yarns used in forming the woven grafts of the present invention may be flat, twisted or textured, and may have high, low or moderate shrinkage properties. Additionally, the yarn type and yarn denier can be selected to meet specific properties desired for the prosthesis such as porosity, flexibility and compliance. The yarn denier utilized in prostheses of the present invention includes a range of deniers from small to heavy.

Although the present invention has been described with reference to particular embodiments, it should be recognized that these embodiments are merely illustrative of the principles of the present invention. Those of ordinary skill in the art will appreciate that the soft-tissue prostheses with seamed transitions of the present invention may be constructed and implemented in other ways and embodiments. Accordingly, the description herein should not be read as limiting the present invention, as other embodiments also fall within the scope of the present invention.

What is claimed is:

1. A woven implantable tubular prosthesis, comprising:
    a plurality of warp yarns and fill yarns;
    a first tubular extent having a first diameter;
    a second tubular extent having a second diameter different from the first diameter;
    a transition tubular extent between the first and second tubular extents, the transition tubular extent having a graduated diameter;
    a tapered edge along the transition tubular extent formed by a weaving pattern having disengagement of a predetermined number of warp yarns forming a graduated change in the number of warp yarns; and
    a seam woven along the tapered edge, wherein the seam provides a substantially fluid-tight transition between the first tubular extent and the second tubular extent.

2. The tubular prosthesis of claim 1, wherein the plurality of warp yarns further comprises top layer warp yarns and bottom layer warp yarns, wherein the seam comprises the top layer warp yarns and the bottom layer warp yarns woven together along the tapered edge.

3. The tubular prosthesis of claim 1, wherein the first tubular extent first diameter and the second tubular extent second diameter is each defined by a different number of warp yarns.

4. The tubular prosthesis of claim 1, further comprising a frustoconical shape, wherein the first tubular extent first diameter is graduated, the second tubular extent second diameter is graduated, and the diameters of the first, second, and transition tubular extents are each graduated in the same direction.

5. The tubular prosthesis of claim 1, further comprising an "S" shape, wherein the tapered edge comprises two opposing edges, the transition tubular extent having a curve in one direction wherein the warp yarns at a first opposing edge are successively disengaged and corresponding warp yarns at a second opposing edge are successively engaged and a curve in the opposite direction wherein the warp yarns at the first opposing edge are successively engaged and corresponding warp yarns at the second opposing edge are successively disengaged.

6. The tubular prosthesis of claim 1, wherein the prosthesis is flat-woven.

7. The tubular prosthesis of claim 1, wherein the warp yarns and fill yarns comprise materials selected from the group consisting of polyester, polypropylene, polyethylene, polyurethane, polytetrafluoroethylene, and mixtures of any thereof.

8. The tubular prosthesis of claim 1, wherein the first, second, and transition tubular extents and the seam are woven.

9. The tubular prosthesis of claim 1, the second tubular extent further comprising two secondary tubular extents that bifurcate from the transition tubular extent, the tapered edge forming a crotch in the transition tubular extent between the two secondary tubular extents by a weaving pattern that disengages a predetermined number of warp yarns in the crotch.

10. The tubular prosthesis of claim 9, wherein the first, second, and transition tubular extents and the seam are woven.

11. The tubular prosthesis of claim 9, wherein each of the two secondary tubular extents has the same diameter.

12. The tubular prosthesis of claim 9, wherein each of the two secondary tubular extents has a different diameter.

13. The tubular prosthesis of claim 1, wherein the first tubular extent comprises a constant first diameter and the second tubular extent comprises a constant second diameter different than the first diameter.

14. A woven implantable tubular prosthesis, comprising:
    a plurality of warp yarns and fill yarns;
    a first tubular extent having a first diameter;

a second tubular extent having a second diameter different from the first diameter;

a transition tubular extent between the first and second tubular extents, the transition tubular extent having a graduated diameter:

a tapered edge along the transition tubular extent formed by a weaving pattern having disengagement of a predetermined number of warp yarns forming a graduated change in the number of warp yarns; and a seam woven along the tapered edge, wherein the seam provides a substantially fluid-tight transition between the first tubular extent and the second tubular extent, and wherein the ratio of disengaged warp yarns to fill yarns causes the tapered edge to have an angle greater than 45 degrees.

15. The tubular prosthesis of claim 14, wherein the ratio of disengaged warp yarns to fill yarns causes the tapered edge to have approximately a 90 degree angle.

16. A woven implantable tubular prosthesis, comprising:

a plurality of warp yarns and fill yarns;

a first tubular extent having a first diameter;

two secondary tubular extents, each having a diameter different than the first tubular extent first diameter;

a transition tubular extent between the first tubular extent and the two secondary tubular extents, the transition tubular extent having a tapered edge and a graduated diameter;

the two secondary tubular extents bifurcating from the transition tubular extent, the tapered edge forming a crotch in the transition tubular extent between the two secondary tubular extents;

the transition tubular extent graduated diameter comprising a weaving pattern that disengages a predetermined number of warp yarns in the crotch; and a seam woven along the crotch, wherein the seam provides a substantially fluid-tight closure in the transition tubular extent.

17. The tubular prosthesis of claim 16, wherein the first tubular extent, the two secondary tubular extents, the transition tubular extent, and the seam are woven together.

18. The tubular prosthesis of claim 17, wherein the plurality of warp yarns further comprises top layer warp yarns and bottom layer warp yarns, wherein the seam comprises the top layer warp yarns and the bottom layer warp yarns woven together along the tapered edge.

* * * * *